United States Patent [19]

Chapman et al.

[11] 4,230,666

[45] Oct. 28, 1980

[54] HYDROCARBON PURIFICATION APPARATUS

[75] Inventors: Charles C. Chapman; Joe Van Pool, both of Bartlesville, Okla.

[73] Assignee: Phillips Petroleum Company, Bartlesville, Okla.

[21] Appl. No.: 923,607

[22] Filed: Jul. 11, 1978

Related U.S. Application Data

[62] Division of Ser. No. 824,583, Aug. 15, 1977, Pat. No. 4,123,351.

[51] Int. Cl.² .................... G05D 9/00; G05D 16/00; G05D 23/00
[52] U.S. Cl. .................................. 422/106; 422/109; 422/111; 422/113; 422/115
[58] Field of Search ............... 422/109, 110, 111, 115, 422/62, 105, 113, 114; 208/262, DIG. 1; 423/240, 488; 585/723

[56] References Cited

U.S. PATENT DOCUMENTS

| | | | |
|---|---|---|---|
| 3,002,818 | 10/1961 | Berger | 422/62 |
| 3,130,187 | 4/1964 | Tolin et al. | 422/111 |
| 3,172,880 | 3/1965 | Lupfer | 422/109 |
| 3,206,390 | 9/1965 | Van Pool | 208/DIG. 1 |
| 3,401,092 | 9/1968 | Matta | 208/DIG. 1 |
| 3,403,198 | 9/1968 | Van Pool | 208/262 |
| 3,451,785 | 6/1969 | Rohlfing et al. | 422/113 |
| 3,547,806 | 12/1970 | Matyear | 208/262 |

FOREIGN PATENT DOCUMENTS 539598  6/1975  U.S.S.R. ................................. 422/111

*Primary Examiner*—S. Leon Bashore
*Assistant Examiner*—Chris Konkol

[57] ABSTRACT

In the removal of HF from hydrocarbon streams by chemical reaction with solid potassium hydroxide, runaway temperatures and subsequent explosions can occur when excess HF is present in the hydrocarbon charged to the KOH treater. According to the invention, a control system and method are provided which regulate the flow of hydrocarbon charged to the KOH treater responsive to temperature changes within the system indicative of excessive amounts of HF in the hydrocarbon stream, thereby preventing the treater temperature from exceeding a preselected maximum allowable value. Several embodiments are provided whereby temperature changes in the KOH treater or a differential temperature across an HF stripper are used as temperature sensing points to control flow of hydrocarbon to the KOH treater.

5 Claims, 3 Drawing Figures

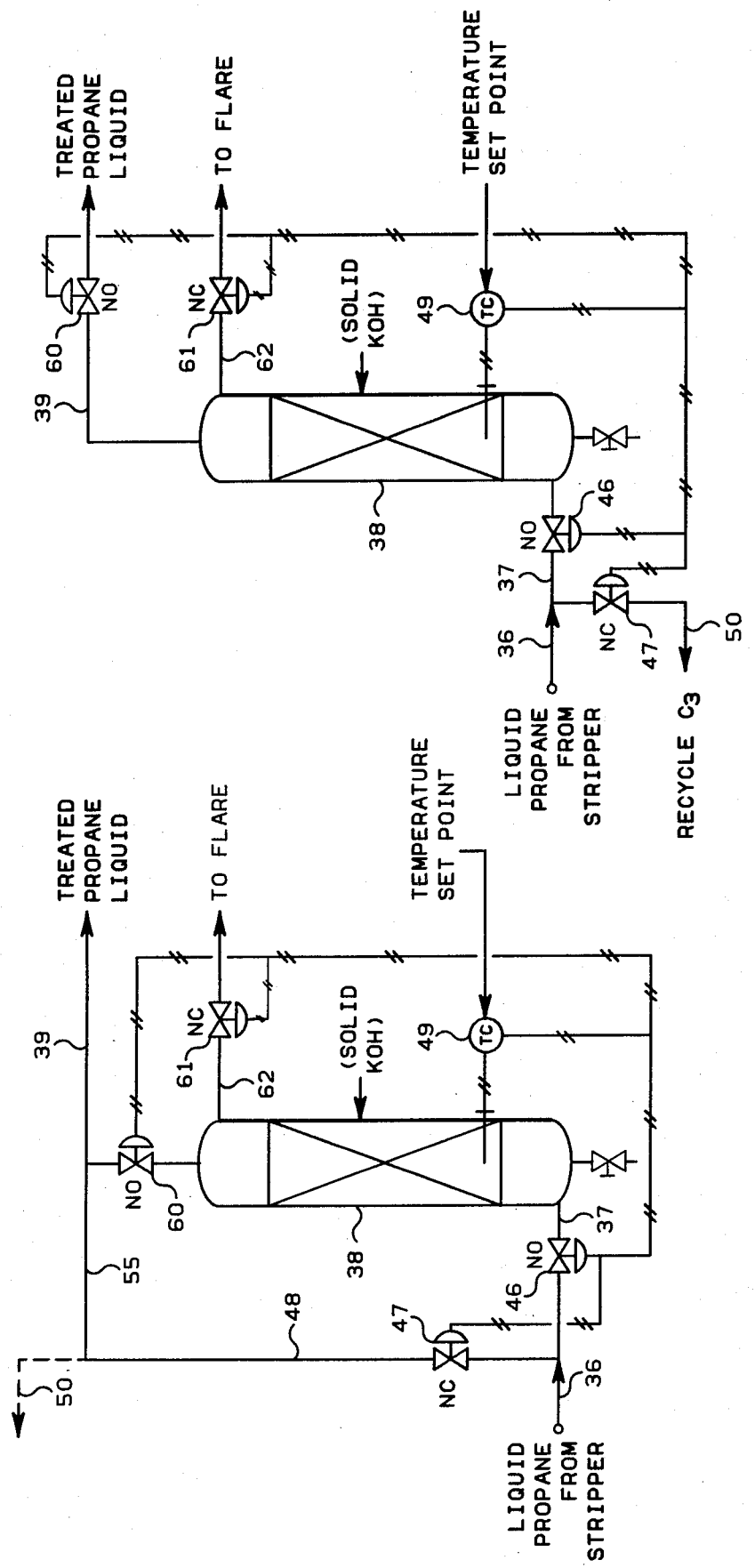

HYDROCARBON PURIFICATION APPARATUS

This application is a division of our copending application having Ser. No. 824,583, filed Aug. 15, 1977 now U.S. Pat. No. 4,123,351 issued Oct. 31, 1978.

This invention relates to the removal of HF from hydrocarbon streams containing same. In accordance with one aspect, this invention relates to the continuous separation of hydrofluoric acid from a hydrocarbon stream employing a solid potassium hydroxide treating agent and the control of separation whereby excessive runaway temperatures are avoided in the KOH treater. In another aspect, this invention relates to a method and apparatus for controlling the purification of a hydrocarbon stream containing HF by contacting with KOH wherein the flow of hydrocarbon charged to the KOH treater is manipulated in response to a preselected maximum allowable temperature within the KOH treatment zone. In accordance with another aspect, this invention relates to a control method and apparatus for purifying a hydrocarbon stream containing HF by contact with KOH wherein the flow of hydrocarbon charged to the KOH treater is manipulated in response to a differential temperature between an intermediate point in an HF stripper and temperature of the effluent stripped material removed from the stripper so that the temperature in the KOH treater does not exceed a preselected maximum allowable temperature.

In a process for the conversion of hydrocarbons wherein liquid hydrogen fluoride (HF) is employed as a catalyst, small amounts of HF acid and organic fluorides are present in the product streams due to the solubility of these materials in hydrocarbons. In most commercial operations, the hydrocarbon phase containing organic fluorides and HF is recontacted with relatively pure liquid HF to remove the organic fluorides therefrom, as described in U.S. Pat. No. 3,254,137, issued May 31, 1966, Hutto et al. In some operations, the propane and normal butane yields are treated with a solid reagent such as bauxite or alumina to remove organic fluorides therefrom as described in U.S. Pat. No. 3,527,840, issued Sept. 8, 1970, to Price. With substantially all of the organic fluorides removed, the propane and the normal butane separate yields can be treated with solid KOH to remove the remaining HF, as described in the above Hutto et al patent. When organic fluorides are not first removed, as above described, then the propane and normal butane yields are each separately treated with solid KOH in the presence of added alcohol as described in U.S. Pat. No. 3,403,198, issued Sept. 24, 1968, to VanPool. This organic fluoride removal, using bauxite or alumina, is effected between the HF stripper and the solid lump KOH treater. KOH removes substantially only HF from the hydrocarbon.

It is necessary to remove the HF from these streams before subsequent processing or blending of the hydrocarbon streams. Normally, the amount of HF present in the hydrocarbon stream is relatively small but the HF still has to be removed from the hydrocarbon streams in order that the hydrocarbons will pass the fluoride specification for the respective streams. Residual amounts of HF are ordinarily removed by contact with solid KOH. Upsets often occur in the processing equipment, thereby causing excess HF in the stream to be charged to the solid bed of KOH particles. When too much HF contacts the KOH, the temperature starts to rise in the bed area due to the heat of reaction between KOH and HF. If excess HF is allowed to continue to flow to the KOH treater, runaway temperatures are experienced which can cause hydrocarbons charged to vaporize and "blow up" the KOH treater with danger then of fires, etc. The present invention is directed to an improved system of controlling the flow of hydrocarbon streams containing HF to a KOH treater in order to prevent runaway temperatures and subsequent explosions.

Accordingly, an object of this invention is to provide an improved method and control system for the removal of HF from hydrocarbon streams.

A further object of this invention is to provide a temperature-sensitive control system for regulating the flow of hydrocarbon streams containing HF to a treater in a practical and economical manner.

A further object of this invention is to provide a sensitive and rapid response control system and method for the purification of hydrocarbon streams.

Other objects, aspects, and the several advantages of this invention will be apparent to those skilled in the art upon a study of the disclosure, the drawings and the appended claims.

In accordance with the invention, a method and a control system are provided for manipulating the flow of hydrocarbon containing HF to a KOH treater whereby the flow of hydrocarbon is regulated responsive to temperatures in the separation system in such a manner that the temperature in the KOH treater does not exceed a preselected maximum allowable value.

In accordance with one embodiment, excessive temperature increases and subsequent explosion in the KOH treater used to remove HF from a hydrocarbon stream, e.g., liquid propane, are avoided by utilizing a preselected maximum differential temperature across the reboiler of an HF stripper to manipulate the control of flow of bottoms charged to the KOH treater or to a bypass around the treater.

A better understanding of the invention will be obtained upon reference to the accompanying drawings wherein:

FIG. 3 and FIG. 4 are alternative embodiments for controlling the flow of hydrocarbon feed to a KOH treater.

Figure 1:
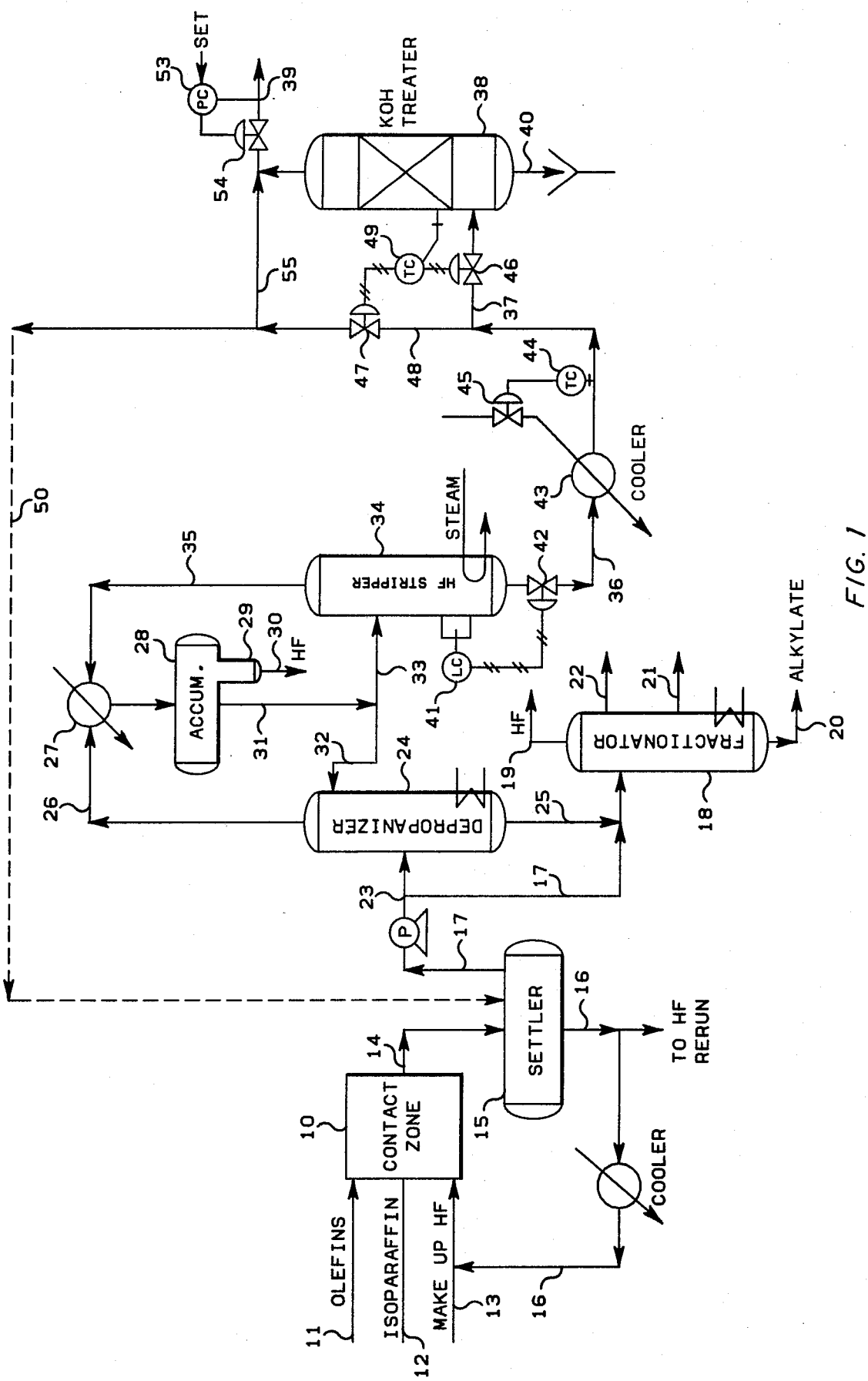
FIG. 1 is a schematic flow diagram of alkylation process and one embodiment of the invention.

In FIG. 1 an alkylation system is illustrated comprising a reactor or contact zone 10 having inlet conduits 11 for olefin such as propylene and/or butylenes, 12 for isoparaffin such as isobutane, and 13 for makeup and rerun hydrogen fluoride (HF) catalyst. Effluent from contact zone 10 is removed via conduit 14 and passed to phase separator or settler 15 wherein the HF phase settles and is removed for recycle via conduit 16 to contact zone 10 with a portion being charged to a rerun system (not shown) for removal of impurities.

The hydrocarbon phase is removed from separation zone 15 by way of line 17 and passed to fractionation zone 18 (which can be a plurality of distillation columns) wherein HF is removed by line 19, alkylate is removed by line 20, normal butane (vapor) is removed by line 21, and isobutane is removed by way of line 22 and recycled (not shown) to contact zone 10.

Propane is often present in the fresh isobutane feed, with propylene feed, and some propane is produced in the process. In order to prevent a buildup of propane in the system, the stream is passed from conduit 17 by way of line 23 to depropanizer 24. Isobutane and heavier are passed by way of line 25 to conduit 17 and then to fractionator 18. Overhead product comprising propane, HF, and alkyl fluorides (when present) is passed by way of line 26 and condenser 27 to phase separator 28. Liquid HF accumulates in sump or leg 29 and is withdrawn by way of line 30. Hydrocarbon liquid, principally propane, containing dissolved HF and alkyl fluoride, e.g., isopropyl fluoride, when present, is withdrawn by way of line 31. A portion of the condensate in 28 is passed by way of line 32 as reflux to depropanizer 24.

The yield portion of the hydrocarbon liquid removed from settler 28 by line 31 is passed by way of line 33 to HF stripper 34 for removal of HF. Overhead product comprising HF and propane passes via conduit 35 and condenser 27 back to phase separator or accumulator 28. Bottoms product comprising propane containing a small or trace amount of HF and, if not previously removed, containing alkyl fluorides (in which case there is a treatment thereof with such as bauxite or alumina upstream, not shown, of the KOH treater) is passed by way of conduits 36 and 37 to contact vessel 38 containing a bed of solid KOH. Propane of very substantially reduced HF content is removed by way of line 39. A slurry of water, KOH, and KOH-HF reaction product (slough) is removed from KOH treater 38 by way of line 40 for disposal or for recovery of KOH. The propane product stream removed overhead from treater 38 by way of line 39 substantially dry and free of HF.

Stripper 34 is operated under conditions sufficient to take overhead most of the HF present in the feed, together with some hydrocarbon, and as bottoms a hydrocarbon stream substantially freed of HF. Stripper 34 can be heated indirectly by steam or other heating medium in a lower portion of the stripper, preferably by indirect heat exchange. In actual operation, for the stripping of HF from a propane stream, the temperature in the upper portion of stripper 34 is ordinarily in the range of about 105° F. to about 140° F. (40°–60° C.), and the bottom temperature is ordinarily about 120° F. to about 155° F. (49°–61° C.). The pressure existing in stripper 34 is ordinarily about 250 psig (1,725 kPa g) to about 350 psig (2,415 kPa g).

The rate of withdrawal of bottoms product (which has been heated indirectly with steam) removed from stripper 34 by way of line 36 is controlled responsive to liquid level controller 41 which manipulates the position of valve 42 in accordance with the desired level of liquid in the bottom of stripper 34. The temperature of the bottoms stream removed from stripper 34 is usually somewhat higher than desired for contact with KOH in treater 38 and, accordingly, is cooled to a temperature of about 100° F. (37.8° C.) in heat exchanger 43. The flow of heat exchange fluid through heat exchanger 43 is controlled by temperature controller 44 which regulates the position of valve 45 responsive to the temperature sensed in line 36 downstream of heat exchanger 43. Normally, the flow of stripped hydrocarbon between stripper 34 and treater 38 is via line 36 and 37 with valve 46 open and valve 47 closed. The temperature is KOH treater 38 is sensed and transmitted to temperature controller 49 which in turn manipulates the position of valves 46 and 47.

In actual operation, the liquid hydrocarbon stream containing residual HF normally charged to KOH treater 38 by way of line 37 is at a temperature of about 100° F. (37.8° C.) and contains small amounts of HF insufficient to cause significant increases of the temperature in the KOH treater. There is a slight warming in the KOH bed when normally small amount of HF, say, about 10 to about 50 ppm, is present in the charge introduced by line 37. When upset occurs with excess HF, as slugs of free HF or, e.g., at least about several hundred ppm, flowing in or with the liquid feed to treater 38, the KOH bed temperature starts to increase rapidly. The temperature control means 49, which senses the temperature in the KOH bed, is set for about 120°–130° F. (49°–54° C.). Thus, when 130° F. (54° C.) is reached, valve 46, which is normally open, is closed, and valve 47, which is normally closed, is opened to allow the high HF-containing stream to be by-passed around KOH treater 38 by way of lines 48 and 55. If desired, an alarm can be sounded, say, at 120°–125° F. (49°–51.78° C.), and the valves can be manipulated as above between 125°–130° F. (51.78°–54° C.). The liquid propane (at about its bubble point) removed from the bottom of stripper 34 is at about 140° F. (60° C.) and a pressure of 285 psig (1,970 kPa g). The pressure in KOH treater 38 is a few pounds lower than in stripper 34, but at 100° F. (37.8° C.) inlet temperature the propane is below its bubble point. In order to prevent vaporization of propane in the KOH unit, a maximum temperature to stop "flashing of liquid to vapor" and resulting disaster is set at about 125°–130° F. (51.78°–54° C.) on temperature control means 49 so that only liquid will be in treater 38.

As a further modification of the flow of FIG. 1, it is within the scope of the invention to pass the stripped hydrocarbon stream around the treater through alternate line 50 for return to settler 15 instead of passing the hydrocarbon stream through by-pass lines 48 and 55. Suitable valves can be provided in line 55 or line 50 can replace line 55 or other modifications can be made as desired.

When pressure in conduit 39 rises to a preset maximum value, pressure controller 53 actuates closing of valve 54 in conduit 39.

Figure 2:
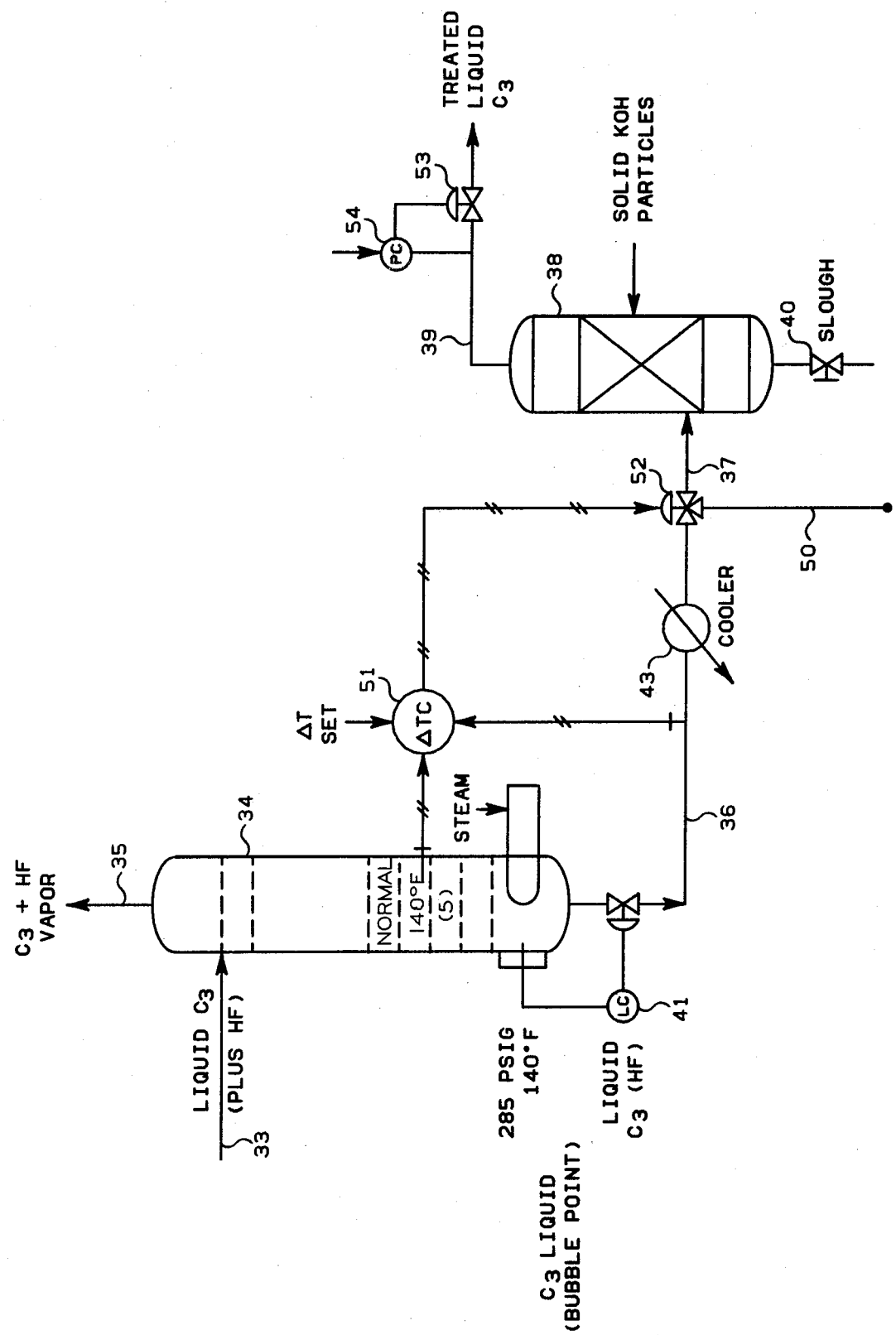
FIG. 2 is a schematic flow diagram of another embodiment of the invention.

In another embodiment of the invention, as illustrated in FIG. 2, stripper 34 and solid KOH treater 38 are positioned as described in connection with FIG. 1. A propane stream 33 is introduced in an upper portion of stripper 34 which is operated under conditions sufficient to take overhead a vapor stream comprising HF and propane by way of line 35. This overhead stream can be returned to condenser 27, as in FIG. 1, for further processing.

A bottoms stream comprising stripped propane and residual HF is removed from stripper 34 by line 36, passed through cooler 43 to reduce the temperature of the stripped steam to about 100° F. (38° C.) for introduction into KOH treater 38 by way of line 37. The rate of withdrawal of bottoms product from column 34 is controlled by liquid level controller 41. The rate of heat exchange fluid passed through exchanger 43 can be controlled by temperature controller (not shown) as described in FIG. 1.

In accordance with this embodiment of the invention, the temperature is sensed at an intermediate point of stripper 34 and in the bottoms product line 36. The temperature sensed at these two points is passed to a differential temperature controller 51 which in turn controls by-pass valve 52. Under normal operating conditions, with small or trace amounts of fluorides in the stripped bottoms stream, the temperature will be about the same at an intermediate point of stripper 34 as bottoms stream 36. However, when excess HF, for example, is included with feed 33 and the HF reaches an intermediate point of column 34, the temperature will drop considerably at this point in stripping zone 34. A drop in temperature at an intermediate point of stripper 34 is indicative of excessive amounts of HF in the system, say, at least about several hundred ppm, including even slugs of free HF therein. Differential temperature controller 51 is set, say, for a differential temperature of 1.0° F. to 2.0° F. (0.5° C. to 1.1° C.), and when this differential is exceeded, differential temperature controller 51 actuates valve 52 to close feed line 37 and pass bottoms product in line 36 through by-pass line 50. Valve 52 is a conventional three-way valve. As shown in FIG. 2, when an upset is experienced with an unexpected excess amount of HF present in the feed to stripper 34, the flow of feed to KOH treater 38 is discontinued and the stripped hydrocarbon stream containing excess HF is passed around treater 38 as described in FIG. 1. Although the by-pass line is shown as line 50 for return of hydrocarbons to settler 15, it is within the scope of the invention to by-pass the hydrocarbon to the effluent line 39 around treater 38.

The conditions obtaining in stripper 34 and treater 38 in this embodiment are essentially as described in connection with FIG. 1.

The fractionation system disclosed in the drawing uses a separate main column 18, along with the depropanizer 34-HF stripper 38 columns. Other conventional fractionation can be used upstream of the HF stripper, e.g., as disclosed in U.S. Pat. No. 3,211,802, issued Oct. 12, 1965, to Dixon et al.

In another embodiment of the invention, as illustrated in FIG. 3, solid KOH treater 38 positioned as described in connection with FIG. 1 is fed with liquid propane containing residual amounts of HF by lines 36 and 37. The hydrocarbon feed introduced into treator 38 is contacted with solid KOH in treater 38 for removal of HF, and the effluent hydrocarbon substantially freed of HF is removed from treater 38 by line 39 for further use as desired. Normally open valve 46 is positioned in line 37, and normally closed valve 47 is positioned in line 48. Normally open valve 60 is in the hydrocarbon outlet line, and normally closed valve 61 is in line 62 passing effluent to flare desired. The temperature in KOH treater 38 is sensed and transmitted to temperature controller 49 which in turn manipulates the position of valves 46, 47, 60, and 61. In the event of excess HF in the feed passed to the treater, the temperature in the treater will increase, and if the temperature exceeds a preset maximum, temperature controller 49 closes valves 46 and 60 and opens valves 47 and 61 so that the feed will by-pass the treater through lines 48, 55, and 39, if desired, or through line 50 for recycle as previously described. In addition, vapors remaining in treater 38 can be vented through line 62.

Referring to FIG. 4, hydrocarbon feed containing HF is passed by way of lines 36 and 37 and introduced into treater 38 for contact with solid KOH to reduce HF content in the feedstream. Treated hydrocarbon is removed by line 39 containing valve 60. Line 62 containing valve 61 is provided for passing vapors from an upper portion of treater 38 to flare if necessary. Valves 46 and 60 are normally open, and valves 47 and 61 are normally closed, as described in FIG. 3. Temperature controller 49 senses the temperature at the inlet portion of the KOH bed and actuates reversal of the valve position of valves 46, 47, 60, and 61 when the temperature rises to above a preset value in order to prevent explosions in the system.

We claim:

1. An apparatus for controlling the separation of HF from hydrocarbons in a manner such that excessive temperature increases above a preselected maximum allowable temperature due to unexpected excess HF is avoided, which apparatus comprises, in combination:

a stripping column having an inlet means for introducing feed into an intermediate portion of the column, an overhead outlet for removing materials stripped from the feed, and a bottom outlet for removing stripped feed containing residual HF and organic fluoride;

a vessel means containing solid KOH and having an inlet for introduction of stripped feed removed from said bottom outlet of said stripping column, an overhead outlet and conduit for removing KOH-treated feed, and a bottom outlet for removing sludge;

first conduit means connected to said bottom outlet of said stripping column and said feed inlet of said vessel means;

heat exchange means in said first conduit means for cooling said stripped feed removed from said stripping column;

by-pass conduit means connected to said first conduit means downstream of said heat exchange means for diverting flow of said stripped feed around said vessel means;

a first flow control valve which is normally open in said first conduit means positioned downstream of said heat exchange means and downstream of the junction point of said by-pass conduit means and said first conduit means and a second flow control valve which is normally closed positioned in said by-pass conduit means downstream of the junction point of said by-pass conduit means and said first conduit means; and a temperature-sensing means in said vessel means connected to said first and said second control valves which are manipulated in response to a preselected maximum allowable temperature within said vessel means and when the measured temperature in said vessel means reaches a preselected maximum value said flow control valve is opened and said first flow control valve is closed so that flow of said stripped feed is diverted to said by-pass conduit means and around said vessel means.

2. An apparatus according to claim 1 wherein the rate of stripped fluid removed from said stripping column is controlled by a liquid controller which adjusts the position of a valve responsive to the liquid level in the bottom of said column, and the temperature of the stream passed through said heat exchange means is controlled responsive to the temperature of the cooled stream downstream of said heat exchange means by regulating the flow of heat exchange fluid passed through said heat exchange means.

3. An apparatus according to claim 1 further comprising:

a flare outlet and conduit connected to an upper portion of said vessel;

a third control valve which is normally open in the conduit connected to said overhead outlet for said vessel;

a fourth control valve which is normally closed in the conduit connected to said flare outlet; and a temperature sensing means in said vessel means connected to said first, second, third, and fourth control valves which are manipulated in response to a preselected maximum allowable temperature in said vessel and when the measured temperature in said vessel reaches the preselected maximum value, said second and fourth flow control valves are opened and said first and third flow control valves are closed.

4. An apparatus for controlling the separation of HF from hydrocarbons in a manner such that excessive temperature increases above a preselected maximum allowable temperature due to unexpected excess HF is avoided, which apparatus comprises, in combination:

a stripping column having an inlet means for introducing feed into an intermediate portion of the column, an overhead outlet for removing materials stripped from the feed, and a bottom outlet for removing stripped feed containing residual HF;

a vessel means containing solid KOH and having an inlet for introduction of stripped feed removed from the bottom outlet of said stripping column, an overhead outlet for removing KOH-treated feed, and a bottom outlet for removing sludge;

first conduit means connected to said bottom outlet of said stripping column and said feed inlet of said vessel means;

heat exchange means in said first conduit means for cooling said stripped feed removed from said stripping column;

a flow control valve positioned downstream of said heat exchange means connected to said first conduit means and a by-pass conduit means at the junction point of said by-pass conduit means and said first conduit means; and a first temperature sensing means at an intermediate point of said stripping column and a second temperature sensing means in said first conduit means positioned upstream of said heat exchange means, a differential temperature controller connected to said first and second temperature sensing means and to said flow control valve, and manipulating the position of said flow control valve in response to a differential temperature in excess of a preset differential temperature and when the temperature differential exceeds the set differential temperature said flow control valve is adjusted so that the flow in said first conduit means to said vessel is discontinued and the flow is diverted through said by-pass conduit means.

5. An apparatus according to claim 4 wherein the rate of stripped fluid removed from said stripping column is controlled by a liquid level controller which adjusts the position of a valve responsive to the liquid level in the bottom of said column, and the temperature of the stream passed through said heat exchange means is controlled responsive to the temperature of the cooled stream downstream of said heat exchange means by regulating the flow of heat exchange fluid passed through said heat exchange means.

* * * * *